United States Patent
Kläui et al.

[11] Patent Number: 6,069,110
[45] Date of Patent: May 30, 2000

[54] BIS- AND TRIS(PYRAZOLYL)BORATE METAL COMPLEX CATALYSTS

[75] Inventors: Wolfgang Kläui, Bloemendalstraat, Switzerland; Bernd Domhöver, Gelsenkirchen, Germany

[73] Assignee: BASF Aktiengesellschaft, Ludwigshafen, Germany

[21] Appl. No.: 09/091,285

[22] PCT Filed: Dec. 19, 1996

[86] PCT No.: PCT/EP96/05715

§ 371 Date: Jun. 16, 1998

§ 102(e) Date: Jun. 16, 1998

[87] PCT Pub. No.: WO97/23492

PCT Pub. Date: Jul. 3, 1997

[30] Foreign Application Priority Data

Dec. 21, 1995 [DE] Germany .................. 195 48 146

[51] Int. Cl.⁷ .................................. C08F 4/642
[52] U.S. Cl. .................. 502/155; 502/202; 526/126; 526/134; 526/160
[58] Field of Search .................. 502/103, 117, 502/134, 152, 155, 202; 526/127, 132, 134, 160, 352, 126; 514/64

[56] References Cited

U.S. PATENT DOCUMENTS

| | | |
|---|---|---|
| 3,984,388 | 10/1976 | Shryne et al. . |
| 4,870,042 | 9/1989 | Kohara et al. . |
| 5,214,126 | 5/1993 | Driessen et al. . |
| 5,519,099 | 5/1996 | Wang et al. .............. 526/132 |
| 5,627,164 | 5/1997 | Gorun et al. .............. 514/64 |

FOREIGN PATENT DOCUMENTS

| | | |
|---|---|---|
| 759 729 | 6/1971 | Belgium . |
| 372 602 | 6/1990 | European Pat. Off. . |
| 1281389 | 7/1972 | United Kingdom . |

OTHER PUBLICATIONS

Rompp Chem. Lexikon, Georg Thieme verl. Stuttgart (1990), S. 2499.
Jr. organometallic Chem.,Bd. 205, 1981, S. 273–279.
Inorganica Chem. Acta, Bd. 244, 1994, S. 131–135.
Drent et al., Ziegler–Natta Catalysts, G. Fink, R. Muhlhaupt, H.H. Brintzinger, 1995, S. 482 ff.
Keim, Angew Chem. (1990), S. 251 ff.

Primary Examiner—Yogendra Gupta
Assistant Examiner—Gregory E. Webb
Attorney, Agent, or Firm—Keil & Weinkauf

[57] ABSTRACT

Metal complexes of the formula (I) or (I') are suitable for the oligomerization and polymerization of olefinically unsaturated compounds and for the copolymerization thereof with carbon monoxide

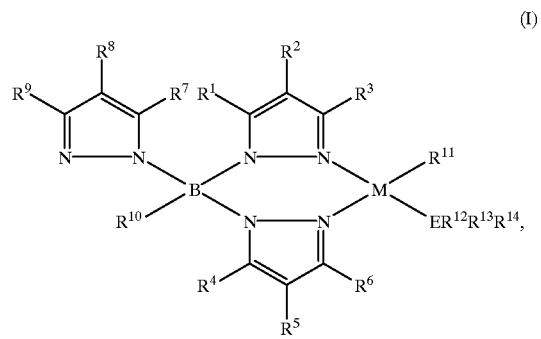

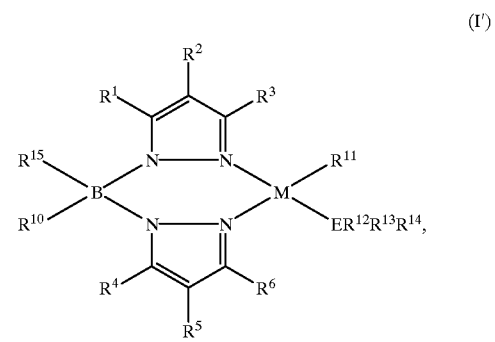

M is a metal from sub-group eight of the Periodic Table of the Elements, E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and $R^{12}$ to $R^{14}$ are substituents selected from the group consisting of $C_1$- to $C_{30}$-organocarbon radicals and $C_3$- to $C_{30}$-organosilicon radicals.

9 Claims, No Drawings

BIS- AND TRIS(PYRAZOLYL)BORATE METAL COMPLEX CATALYSTS

This application claims priority from PCT international application 96/05715 filed Dec. 19, 1996 and from Federal Republic of Germany 19548146.1 filed Dec. 21, 1995.

The present invention relates to metal complexes of the formulae (I) and (I') which are suitable for the oligomerization and polymerization of olefinically unsaturated compounds and for the copolymerization thereof with carbon monoxide

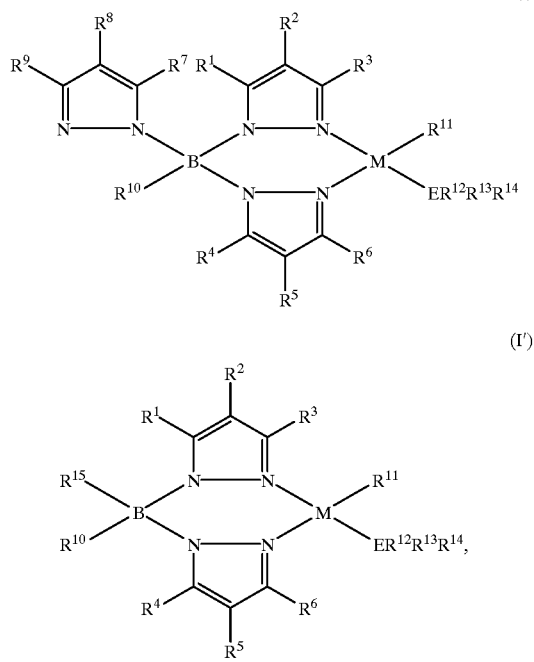

where

M is a metal from sub-group eight of the Periodic Table of the Elements,

E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and $R^{12}$ to $R^{14}$ are substituents selected from the group consisting of $C_1$- to $C_{30}$-organocarbon radicals and $C_3$- to $C_{30}$-organosilicon radicals, and to catalyst systems which are suitable for the oligomerization and polymerization of olefinically unsaturated compounds and the copolymerization thereof with carbon monoxide, comprising, as active constituents, A) a metal complex of the formula (I)

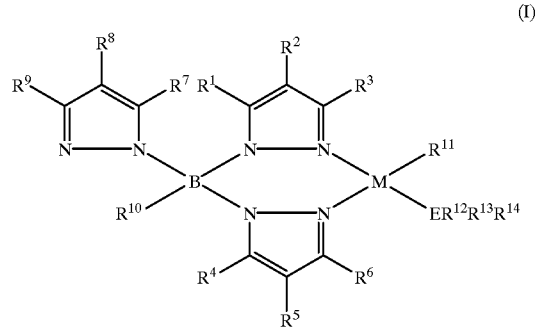

or a metal complex of the formula (I')

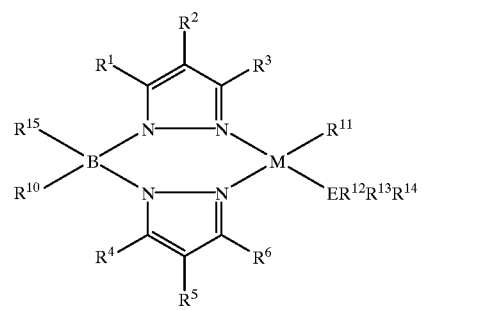

where

M is a metal from sub-group eight of the Periodic Table of the Elements,

E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and $R^{12}$ to $R^{14}$ are substituents selected from the group consisting of $C_1$- to $C_{30}$-organocarbon radicals and $C_3$- to $C_{30}$-organosilicon radicals, and B) a Lewis acid.

The present invention furthermore relates to a process for the preparation of metal complexes of the formula (I)

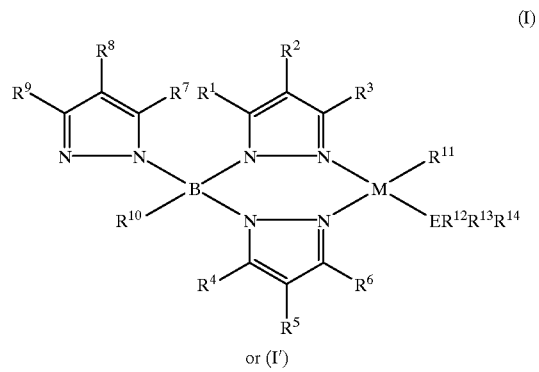

-continued

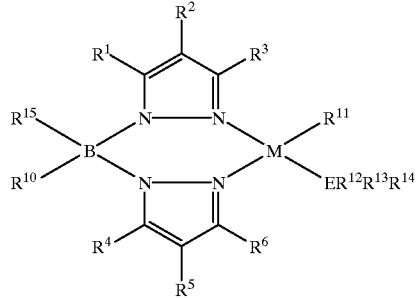
(I')

by reacting a halometal complex of the metal with a tris(pyrazolyl)borate anion of the formula (II)

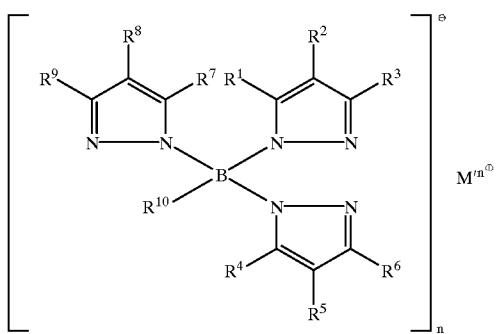
(II)

or with a bis(pyrazolyl)borate anion of the formula (II')

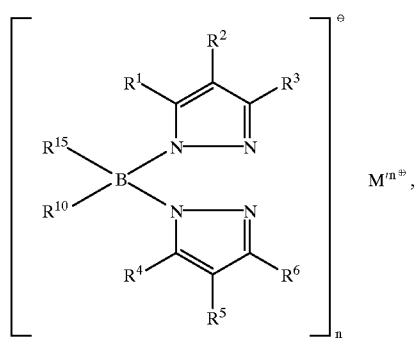
(II'), where, in (I), (I'), (II) or (II'),

M is a metal from sub-group eight of the Periodic Table of the Elements,

M' is lithium, sodium, potassium, rubidium, cesium, magnesium, calcium or thallium, E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, $R^{12}$ to $R^{14}$ are substituents selected from the group consisting of $C_1$- to $C_{30}$-organocarbon radicals and $C_3$- to $C_{30}$-organosilicon radicals, and n is 1 or 2, where n is the formal valence of M', to a process for the preparation of oligomers and polymers of olefinically unsaturated compounds and of copolymers of olefinically unsaturated compounds and carbon monoxide by polymerizing the monomers at from 0 to 300° C. and from 1 to 500,000 kPa in the presence of a metal complex of the formula (I)

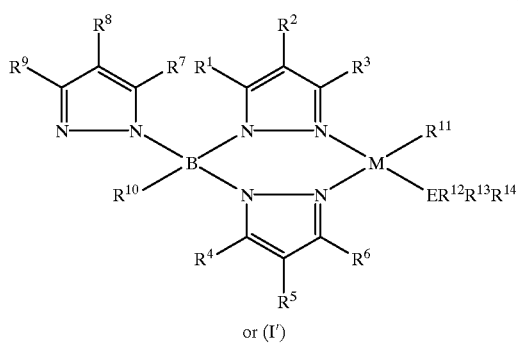
(I)

or (I')

(I')

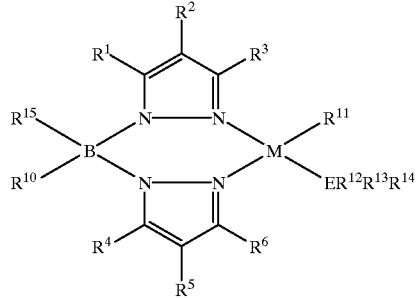

where

M is a metal from sub-group eight of the Periodic Table of the Elements,

E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and $R^{12}$ to $R^{14}$ are substituents selected from the group consisting of $C_1$- to $C_{30}$-organocarbon radicals and $C_3$- to $C_{30}$-organosilicon radicals, and to a process for preparation of oligomers and polymers of olefinically unsaturated compounds and of copolymers of olefinically unsaturated compounds and carbon monoxide by polymerizing the monomers at from 0 to 300° C. and from 1 to 500,000 kPa in the presence of a catalyst system comprising, as active constituents, A) a metal complex of the formula (I)

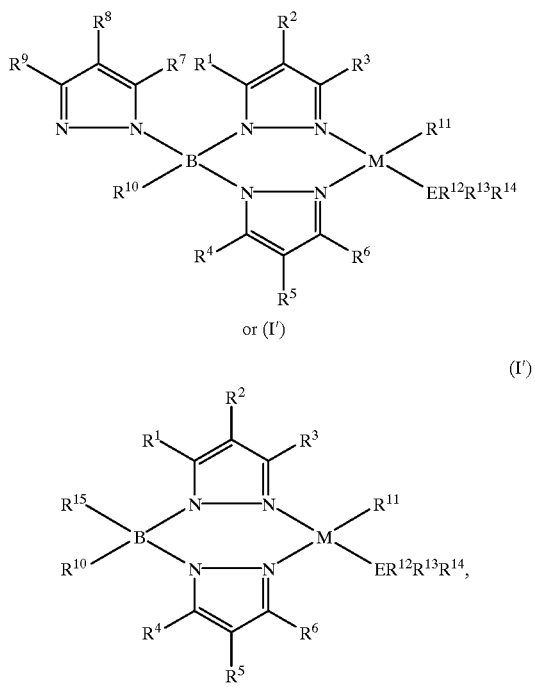

or (I')

where
- M is a metal from sub-group eight of the Periodic Table of the elements,
- E is an element from main group five of the Periodic Table of the elements,
- $R^1$ to $R^{11}$, $R^{15}$ are substituents selected from the group consisting of hydrogen, $C_1$- to $C_{30}$-organocarbon radicals and $C_3$- to C30-organosilicon radicals, and
- $R^{12}$ to $R^{14}$ substituents selected from the group consisting of $C_1$- to $C_{30}$-organocarbon radicals and $C_3$- to $C_3$—organosilicon radicals, and B) a Lewis acid.

The present invention furthermore relates to the use of a metal complex of the formulae (I) and (I') as claimed in claim 1 as catalyst for the preparation of oligomers and polymers of olefinically unsaturated compounds and for the preparation of copolymers of olefinically unsaturated compounds and carbon monoxide, and to the use of a catalyst system as claimed in claim 4 for the preparation of oligomers and polymers of olefinically unsaturated compounds and for the preparation of copolymers of olefinically unsaturated compounds and carbon monoxide.

Metal complexes of metals from sub-group eight of the Periodic Table of the Elements have hitherto, such as nickel, been used in olefin oligomerizations (W. Keim, Angew. Chem. (1990), pages 251 ff) or in olefin-carbon monoxide copolymerizations, palladium (E. Drent et al., in "Ziegler-Natta Catalysts", G. Fink, R. Mühlhaupt, H. H. Brintzinger (editors), Springer Verlag, Berlin (1995), pages 482 ff) or nickel (U.S. Pat. No. 3,984,388; U.S. Pat. No. 5,214,126).

However, none of the metal complexes or catalysts employed was free from disadvantages; either they were complicated to prepare, expensive, had unsatisfactory activity or required excessively high polymerization temperatures or pressures.

It is an object of the present invention to provide metal complexes of the formulae (I) and (I') and catalyst systems containing (I) or (I') which do not have the abovementioned disadvantages, or only do so to a minor extent, have high productivity and are easily accessible. A further object of the present invention was to provide a process for the preparation of the metal complexes of the formulae (I) and (I') and a process for the preparation of oligomers and polymers of olefinically unsaturated compounds and a process for the preparation of copolymers of olefinically unsaturated compounds and carbon monoxide in the presence of the metal complexes of the formulae (I) and (I') or in the presence of the catalyst systems, and the use of the metal complexes of the formula (I) or (I') or of the catalyst systems for the preparation of oligomers and polymers of this type.

We have found that this object is achieved by the metal complexes of the formulae (I) and (I') defined at the outset and by the catalyst systems defined at the outset, by a process for the preparation of the metal complexes of the formulae (I) and (I'), by a process for the preparation of oligomers and polymers of olefinically unsaturated compounds and of copolymers of olefinically unsaturated compounds and carbon monoxide in the presence of the metal complexes of the formulae (I) or (I') or in the presence of the catalyst systems defined at the outset, and by the use of the metal complexes of the formulae (I) and (I') and by the use of the catalyst systems defined at the outset for the preparation of oligomers and polymers of olefinically unsaturated compounds or for the preparation of copolymers of these compounds and carbon monoxide.

Suitable metals M in the metal complexes of the formulae (I) and (I') are those from sub-group eight (VIIIB) of the Periodic Table of the Elements, i.e. iron, cobalt, ruthenium, rhodium, osmium, iridium, platinum, palladium and very particularly nickel. In the complexes, the metals can formally have a double positive charge.

Suitable elements E are those from main group V (group VA), of the Periodic Table of the Elements, i.e. nitrogen, phosphorus, arsenic, antimony or bismuth. Nitrogen and phosphorus, in particular phosphorus, are particularly suitable.

The radicals $R^1$ to $R^{11}$ and $R^{15}$ can be hydrogen or organocarbon or organosilicon radicals. Suitable organocarbon radicals $R^1$ to $R^{11}$ and $R^{15}$ are aliphatic, cycloaliphatic and very particularly aromatic radicals, in each case having 1 to 30 carbon atoms.

Radicals which may be mentioned by way of example are linear and preferably branched $C_1$- to $C_{10}$-alkyl groups, such as methyl, ethyl, 1-propyl, isopropyl, 1-butyl, sec-butyl, tert-butyl and 1-hexyl. Suitable cycloaliphatic radicals which may be mentioned are $C_3$- to $C_6$-cycloalkyl radicals, such as cyclohexyl.

Particularly suitable organocarbon radicals $R^1$ to $R^{11}$ and $R^{15}$ are aromatic radicals, which may also be substituted, for example by $C_1$- to $C_6$-alkyl radicals, by further $C_6$-$C_{10}$-aryl radicals or by halogens, such as fluorine, chlorine, bromine or iodine, or alternatively by perfluoroalkyl radicals, such as trifluoromethyl, pentafluoroethyl, heptafluoropropyl or heptafluoroisopropyl radicals. If the aryl radicals do not carry any further carbon substituents, they preferably contain 6 to 20 carbon atoms. Alkylaryl radicals $R^1$ to Rll which are substituted by alkyl groups or derivatives thereof preferably have 1 to 10 carbon atoms in the alkyl radical and 6 to 10 carbon atoms in the aryl radical.

The aromatic ring may of course also be substituted a number of times.

Examples which may be mentioned of highly suitable radicals $R^1$ to $R^{11}$ are phenyl, 1-naphthyl, 2-naphthyl, ortho-tolyl, meta-tolyl, p-tolyl, 2,4,6-trimethylphenyl (mesityl), 2-(trifluoromethyl)-phenyl, 2,6-di(trifluoromethyl)phenyl, 2,6-dimethylphenyl and 2,4-dimethylphenyl.

Suitable organosilicon radicals $R^1$ to $R^{11}$ and $R^{15}$ having 3 to 30 carbon atoms are preferably triorganosilyl radicals containing $C_1$- to $C_{10}$-alkyl radicals or $C_6$–$C_{10}$-aryl radicals, such as trimethylsilyl, triethylsilyl, triphenylsilyl or tert-butyldimethylsilyl.

The radicals $R^{12}$, $R^{13}$ and $R^{14}$ can have the same meaning as the organocarbon and organosilicon radicals $R^1$ to $R^{11}$. However, the radicals $R^{12}$, $R^{13}$ and $R^{14}$ are generally not hydrogen.

Metal complexes of the formulae (I) and (I') which have proven very highly suitable are those in which $R^{11}$, $R^{12}$, $R^{13}$, $R^{14}$, $R^3$ and $R^6$ and in some cases also $R^9$ are aromatic radicals of the types specified above for these substituents, preferably phenyl or ortho-tolyl, and in which $R^{10}$, $R^{15}$ and the substituents on the pyrazolyl rings $R^1$, $R^2$, $R^4$, $R^5$, $R^7$ and $R^8$ are hydrogen.

Examples of very particularly preferred metal complexes of the formulae (I) and (I') are
[(hydrotris(3-phenylpyrazolyl)borato)(ortho-tolyl)(triphenylphosphine)]nickel(II),
[hydrotris(3-p-tolylpyrazolyl)borato)(ortho-tolyl)(triphenylphosphine)]nickel(II) and
[hydrotris(3-phenylpyrazolyl)borato)(ortho-tolyl)(tri(p-tolyl)phosphine)]nickel(II).

A particularly preferred metal complex of the formula (I') is [{dihydrobis(3-phenylpyrazolyl)borato}(ortho-tolyl)(triphenylphosphine)]nickel(II).

It has proven advantageous to react the novel metal complexes of the formulae (I) and (I') with a compound B) which is capable of binding the ligand $ER^{12}R^{13}R^{14}$ more strongly than can the metal M.

Compounds which are suitable for this purpose are generally Lewis acids, which, according to Römpps Chemie Lexikon, Georg Thieme Verlag, Stuttgart, New York, (1990), page 2499, represent electron-pair acceptors.

The chemical nature of the Lewis acids B) is generally not important. Suitable compounds are the halides of magnesium, boron, aluminum, gallium, silicon, germanium, tin, phosphorus, arsenic, antimony, titanium, zirconium and hafnium, the metals preferably being in their highest formal oxidation state.

Further suitable Lewis acids are carbocation salts, such as triphenylmethyl tetrafluoroborate.

Examples which may be mentioned of particularly suitable Lewis acids are boron trifluoride, boron trifluoride diethyl ether complex, boron tribromide, tris(pentafluorophenyl)boron, aluminum trichloride and magnesium dichloride.

Good results, in particular in the oligomerization and polymerization of olefinically unsaturated compounds, have been achieved using boron trifluoride diethyl ether complex as component B).

The molar ratio between component A) and the Lewis acid B) is generally from 0.01:1 to 1:1, preferably from 0.02:1 to 1:1.

As component A), the catalyst systems can of course also contain mixtures of different metal complexes of the formula (I) or (I').

The novel metal complexes of the formulae (I) and (I') are advantageously prepared by substitution of a halogen atom, i.e. fluorine, chlorine, bromine or iodine, in a halogen-metal complex of the metals M by a bis- or tris(pyrazolyl)borato ligand.

To this end, a main-group metal compound of the formula (II)

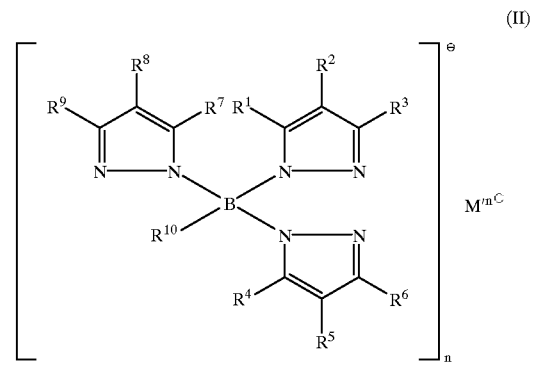

or (II')

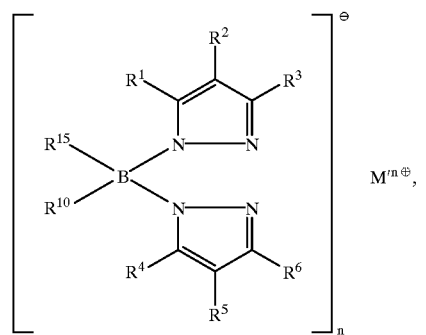

where M' is lithium, sodium, potassium, rubidium, cesium, magnesium, calcium or preferably thallium, n, as the formal valence of M', is 1 or 2, and $R^1$ to $R^{15}$ are as specified above under the formulae (I) or (I'), is usually reacted with a halogen-metal complex of the metal M, in particular of nickel or palladium, preferably in an organic solvent, such as dichloromethane, toluene, tetrahydrofuran or diethyl ether.

Mixtures of solvents, for example acetone/dichloromethane, are also preferably used for the preparation of the metal complexes of the formula (I').

The halogen-metal complex used is preferably one of the formula $M(ER^{12}R^{13}R^{14})_2(R^{11})\times(III)$, where M, E and $R^{11}$ to $R^{14}$ are as defined above under the formula (I) or (I'), and X is fluorine, chlorine, bromine or iodine, preferably chlorine or bromine.

The reaction is generally carried out at from (–)80° C. to 200° C., preferably at from 0° C. to 110° C.

The novel metal complexes of the formula (I) or (I') and the catalyst systems can be used for the preparation of oligomers and polymers of olefinically unsaturated compounds and for the preparation of copolymers, generally alternating copolymers, of olefinically unsaturated monomers and carbon monoxide (polyketones).

Suitable olefinically unsaturated compounds are in principle all monomers from this class of compounds.

Preference is given to ethylene and $C_3$- to $C_{10}$-alk-1-enes, such as 1-butene, 1-hexene and principally propene, and furthermore butadiene, and also cycloolefins, such as cyclopentene, cyclohexene, norbornene and norbornadiene and its derivatives. olefinically unsaturated aromatic monomers which may be mentioned are primarily styrene and α-methylstyrene.

Also of importance are acrylic acid and methacrylic acid, and derivatives thereof, in particular the nitriles, the amides and the $C_1$-$C_6$-alkyl esters, for example ethyl acrylate, n-butyl acrylate, tert.-butyl acrylate and methyl methacrylate.

Further suitable monomers are vinyl chloride, vinyl acetate, vinyl propionate, maleic anhydride and N-vinylpyrrolidone.

It is of course also possible to employ mixtures of different monomers, the mixing ratio generally not being important.

The molar ratio between the olefinically unsaturated compounds, preferably ethylene, propene, 1-butene or 1-hexene, and carbon monoxide can be chosen substantially freely and is preferably from 0.01:1 to 100:1, preferably in the region of 1:1.

The polymerizations for the preparation of the oligomers and polymers of olefinically unsaturated compounds and of the carbon monoxide copolymers can be carried out either batchwise or continuously.

Pressures of from 1 to 500000 kPa, preferably from 200 to 350000 kPa, in particular from 500 to 30000 kPa, and temperatures of from 0 to 300° C., preferably from 20 to 250° C., in particular from 40 to 150° C., have proven suitable.

Polymerization reactions using the metal complexes of the formula (I) or (I') or catalyst systems defined at the outset can be carried out in the gas phase, in suspension, in liquid or supercritical monomers and in solvents which are inert under the polymerization conditions.

Suitable inert solvents are alcohols, such as methanol, ethanol, propanol, i-propanol, 1-butanol and tert.-butanol, sulfoxides and sulfones, for example dimethyl sulfoxide, esters, such as ethyl acetate and butyrolactone, ethers, such as tetrahydrofuran, dimethylethylene glycol and diisopropyl ether, and preferably aromatic solvents, such as benzene, toluene, ethylbenzene and chlorobenzene, or mixtures thereof.

The molecular weight of the novel polymers can be influenced in a manner known to the person skilled in the art by varying the polymerization temperature, by means of protic compounds, such as alcohols, for example methanol, ethanol or tert.-butanol, preferably methanol, and by adding hydrogen. In general, a high concentration of regulating substances and/or a high polymerization temperature produce a relatively low molecular weight, and vice versa.

The oligomers, preferably those of $C_2$- to $C_{10}$-alk-1-ene, such as ethylene and propene, generally have a degree of polymerization, determined by $^{13}$C-NMR end-group analysis, of from 2 to 1000, preferably from 2 to 100, in particular from 2 to 50.

The high polymers, preferably those of $C_2$- to $C_{10}$-alk-1-enes, such as ethene, propene, 1-butene, 1-hexene and 1-octene, generally have a molecular weight Mw, determined by gel permeation chromatography at 135° C. in 1,2,4-trichlorobenzene compared with polyethylene standard, in the range from 30000 to 3000000 and an Mw/Mn in the range from 1.5 bis 5.0.

The molecular weights Mw (weight average) of the carbon monoxide copolymers (measured by gel permeation chromatography (GPC) at 25° C. using Shodex® HFIP 803 or 805 as column material and hexafluoroisopropanol as solvent against polymethyl methacrylate standard) are generally in the range from 1000 to 1000000, preferably from 1000 to 100000.

The molecular weight distribution Mw/Mn (weight average/number average), measured by gel permeation chromatography (GPC) as described above, of the carbon monoxide copolymers is generally from 1 to 50, preferably from 1 to 20.

Owing to their numerous functional groups, the novel carbon monoxide copolymers can be modified using conventional chemical reactions, as described, for example, in EP-A 372 602, or a combination of the two methods.

EXAMPLES

Example 1

Synthesis of [{hydrotris(3-phenylpyrazolyl)borato}(ortho-tolyl)(triphenylphosphine)]nickel(II)

2.00 g (2.7 mmol) of [NiBr(o-tol)(PPh$_3$)$_2$] were dissolved in 25 ml of dichloromethane at room temperature under a nitrogen atmosphere, and 1.71 g (2.7 mmol) of [Tl{HB(3-Ph-pyrazolyl)$_3$}] were added. The solution was stirred for 60 minutes, and the TlBr formed was filtered off. 10 ml of hexane were added, and the solution was concentrated to about 5 ml under reduced pressure, and the resultant yellow solid was washed with a little hexane until the solvent remained colorless. The complex was then dissolved in a little toluene, the solution was filtered, 10 ml of hexane were added, and the mixture was evaporated to dryness. The analytically pure product was recrystallizable from diethyl ether. Yield: 1.89 g (82%).

$^1$H-NMR (CDCl$_3$): 1.60 ppm (S, 3H, CH$_3$-tolyl), 5.51 ppm (dt, 1H, tolyl), 5.78 ppm (d, 1H, pz, $^3J^{HH}$~2.3 Hz), 6.04 ppm (d, 1H, PZ, $^3J^{HH}$~2.1 Hz), 6.20 ppm (m, 2H, tolyl), 6.52 ppm (d, 2H, J 8.1 Hz), 6.69 ppm (m, 6H), 6.87 ppm (d, 1H, pz, $^3J^{HH}$~2.1 Hz), 7.06 ppm (m, 6H), 7.41 ppm (m, 19H), 8.01 ppm (d, 2H, J~7.2 Hz), 8.28 ppm (d, 1H, pz, $^3J^{HH}$~2.2 Hz) (d$_8$-toluene): 2.13 ppm (s, 3H, CH$_3$-tolyl), 5.83 ppm (d, 1H, pz, $^3J^{HH}$~2.1 Hz), 6.51 ppm (m, 2H, tolyl), 6.94–7.61 ppm (m, H), 7.81 ppm, (m, H), 8.36 ppm (d, 2H, J~7.1 Hz), 8.42 ppm (d, 1H, pz, $^3J^{HH}$~2.2 Hz)

$^{13}$C{$^1$H}-NMR: 23.2 ppm, 103.1 ppm, 106.3 ppm, 107.1 ppm, 119.8 ppm, 122.7 ppm, 126.7 ppm, 127.7 ppm (d, J$_{PC}$~13.9 Hz), 128.0 ppm, 128.2 ppm (d, J$_{PC}$~9.7 Hz), 128.5 ppm, 129.1 ppm, 129.3 ppm, 130.0 ppm, 130.1 ppm, 130.4 ppm, 130.7 ppm, 134.5 ppm (d, J$_{PC}$~9.8 Hz), 135.0 ppm, 135.1 ppm, 135.4 ppm, 135.7 ppm, 139.6 ppm, 140.1 ppm (d; J$_{PC}$~5.2 Hz), 146.3 ppm. $^{31}$P{1H}-NMR: 18.4 ppm (s) IR (KBr): 2382 v(BH) w, 1468 w, 1438 w, 1433 w, 1371 w, 1280 w, 1207 m, 1180 w, 1103 w, 1088 w, 1070 w, 1051 w, 1038 w, 751 s, 736 w, 696 s, 530 m.

| Elemental analysis: (C$_{52}$H$_{44}$N$_6$BPNi) (C$_4$H$_{10}$O), | | |
|---|---|---|
| calculated: C 72.51 | H 5.87 | N 9.06; |
| found: C 72.12 | H 5.81 | N 9.07. |

Examples 2 to 4

Catalytic oligomerizations 102 mg (0.12 mmol) of [(hydrotris(3-phenylpyrazolyl)borato)(ortho-tolyl)(triphenylphose)]nickel(II) were dissolved in 50 ml of toluene, 0.6 ml mmol, B:Ni=35:1) of boron trifluoride diethyl ether complex added if desired, and the mixture was then oligomerized for ours under a monomer pressure of 4000 kPa.

The reaction products were analyzed by gas chromatography (GC/MS coupling) (column: Ultra 2 crosslinked, coated with 5% of phenyl silicone, 95% of methyl silicone; 25 m×0.2 mm; 50 to 200° C.; 5° C./min; nitrogen carrier gas).

The experiment parameters and results are shown in Table 1.

TABLE 1

Oligomerization of alkenes

| Example | Addition, ml | Monomer | Pressure (kPa) | Temperature (° C.) | Product |
|---|---|---|---|---|---|
| 2 | — | Ethylene | 4000 | 60 | $C_4H_8$ to $C_{22}H_{44}$ |
| 3 | $BF_3$ diethyl ether; 0.6 | Ethylene | 4000 | 20 | $C_4H_8$ to $C_{12}H_{24}$ |
| 4 | $BF_3$ diethyl ether; 0.65 | Propene | 1000 | 20 | $C_6H_{12}$ to $C_{15}H_{30}$, 12 ml |

Example 5

Polyketone preparation 102 mg (0.12 mmol) of [(hydrotris(3-phenylpyrazolyl)-borato)(ortho-tolyl)(triphenylphosphine)]nickel(II) in 50 ml of toluene were reacted for 16 hours at 60° C. in the presence of 0.3 mol of ethylene (4000 kPa) and 14.3 mmol of carbon monoxide (350 kPa). The solvent was then removed, giving 1.15 g of polyketone (IR: $V_{C=O}$=1691, $^{13}$C-NMR: 36.4 ppm, singlet; 212.7 ppm, singlet. $M_w$=5770, Mw/Mn=1.3).

Example 6

Synthesis of [{dihydrobis-3-phenylpyrazolyl)borato}(ortho-tolyl)(triphenylphosphine)nickel(II)]

Equimolar amounts of K[$H_2$B(3-Ph-pyrazolyl)$_2$](223.9 mg, 0.66 mmol) and [NiBr(o-tol)(PPh$_3$)$_2$](500.0 mg, 0.66 mmol) were stirred in a mixture of acetone/dichloromethane (15 ml/15 ml) under nitrogen for 16 hours. The resulting precipitate was filtered off and the filtrate, following the addition of about 5 ml of n-hexane, was concentrated under reduced pressure to 5 ml, in the course of which a yellow precipitate was produced which was washed with a little hexane until the solvent remained pale yellow to colorless. The precipitate was dried under reduced pressure and subsequently washed a number of times with a little acetone in order to remove paramagnetic impurities. The product was dried under reduced pressure. Yield: 130 mg (28%)

$^1$H-NMR (CDCl$_3$): 2.20 ppm (s, 3H, CH$_3$, o-tol), 5.70 ppm (d, 1H, pz, $3J_{HH}$~2,3 Hz), 6.00 ppm (d, 2H, o-tol, $^3J_{HH}$~6.4 Hz), 6.25–6.37 ppm (m, 3H, o-tol), 7.01 ppm (d, 1H, pz, $^3J_{HH}$~2.2 Hz), 7.1–8.3 ppm (d+m+d, 27H, PPh$_3$, pz, Ph); $^{31}$P{$^1$H}-NMR (CDCl$_3$): 22.56 ppm (s, PPh$_3$); IR (KBr): 2420 cm$^{-1}$ vBH)

Example 7

Polyketone preparation 56 mg (0.10 mmol) of [{dihydrobis-3-phenylpyrazolyl) borato}-(ortho-tolyl)(triphenylphosphine)nickel(II)] were dissolved in 10 ml of toluene and the solution was stirred in an autoclave (100 ml) under an ethene pressure of 40 bar and a carbon monoxide pressure of 3.5 bar at 60° C. for 16 hours. The precipitated polyketone was filtered off and washed with tetrahydrofuran. Yield: 1.05 g

We claim:

1. A metal complex of the formula (I) or (I') which is suitable for the oligomerization and polymerization of olefinically unsaturated compounds and for the copolymerization thereof with carbon monoxide

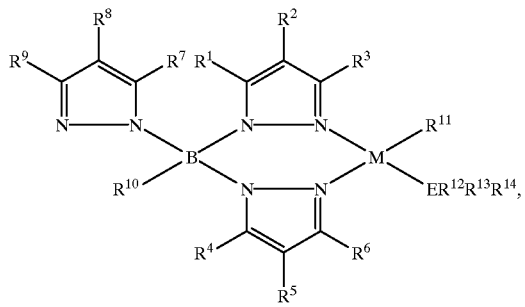
(I)

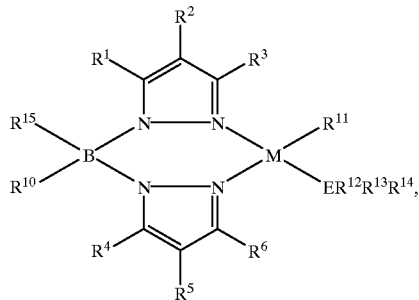
(I')

where

M is a metal from sub-group eight of the Periodic Table of the Elements,

E is an element from main group five of the Periodic Table of the Elements, $R^1$ to $R^{10}$, $R^{15}$ are substituents selected from the group consisting of hydrogen, $C_1$- to $C_{30}$-organocarbon radicals and $C_3$- to $C_{30}$-organosilicon radicals, $R^{11}$ is hydrogen, or is $C_6$- to $C_{20}$-aryl or $C_7$- to $C_{30}$-alkylaryl having 1 to 10 carbon atoms in the alkyl radical and 6 to 10 carbon atoms in the aryl radical, or is a $C_3$- to $C_{30}$-organosilicon radical, and $R^{12}$ to $R^{14}$ are substituents selected from the group consisting of $C_1$- to $C_{30}$-organocarbon radicals and $C_3$- to $C_{30}$-organosilicon radicals.

2. A catalyst system which is suitable for the oligomerization and polymerization of olefinically unsaturated compounds and the copolymerization thereof with carbon monoxide, comprising, as active constituents, A) a metal complex of the formula (I)

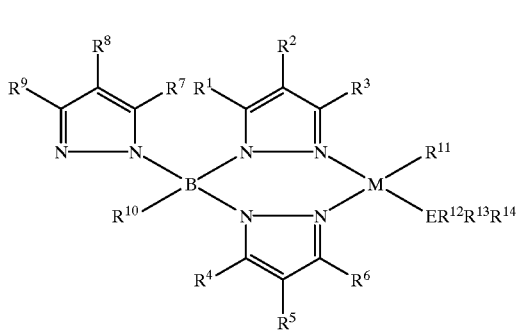
(I)

or a metal complex of the formula (I')

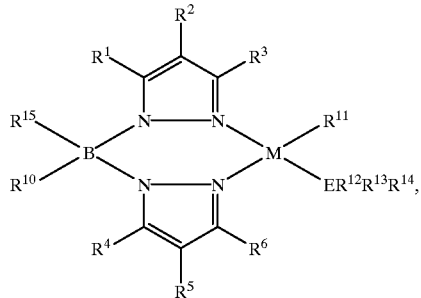
(I')

where

M is a metal from sub-group eight of the Periodic Table of the Elements,

E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and $R^{12}$ to $R^{14}$ are substituents selected from the group consisting of $C_1$- to $C_{30}$-organocarbon radicals and $C_3$- to $C_{30}$-organosilicon radicals, and B) a Lewis acid.

3. A process for the preparation of a metal complex of the formula (I)

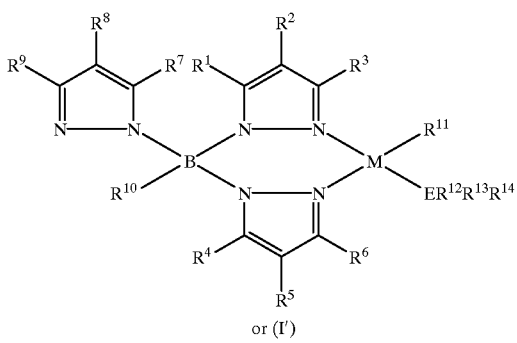
(I)

or (I')

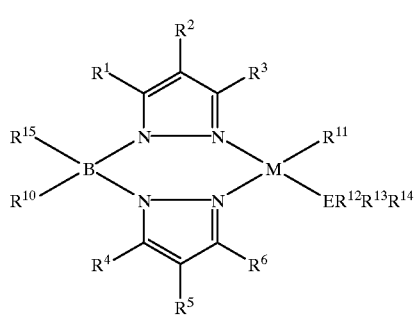
(I')

by reacting a halometal complex of the metal with a tris-(pyrazolyl)borate anion of the formula (II)

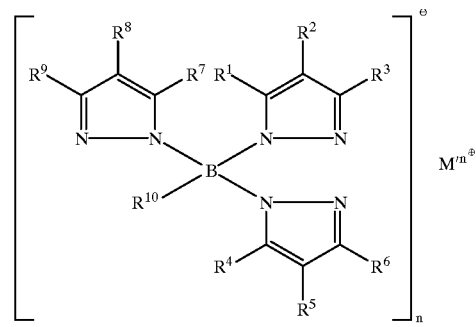
(II)

or with a bis(pyrazolyl)borate anion of the formula (II')

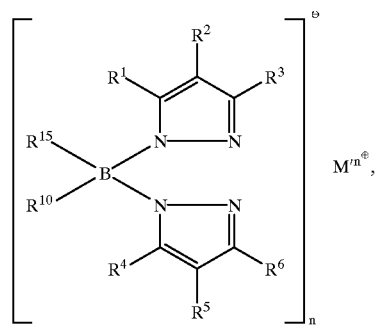
(II')

where, in (I), (I'), (II) or (II'),

M is a metal from sub-group eight of the Periodic Table of the Elements,

M' is lithium, sodium, potassium, rubidium, cesium, magnesium, calcium or thallium, E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, $R^{12}$ to $R^{14}$ are substituents selected from the group consisting of $C_1$- to $C_{30}$-organocarbon radicals and $C_3$- to $C_{30}$-organosilicon radicals, and n is 1 or 2, where n is the formal valence of M'.

4. A process for the preparation of oligomers and polymers of olefinically unsaturated compounds and of copolymers of olefinically unsaturated compounds and carbon monoxide by polymerizing the monomers at from 0 to 300° C. and from 1 to 500,000 kPa in the presence of a metal complex of the formula (I)

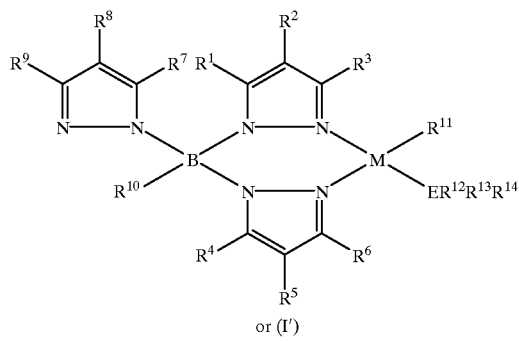

or (I')

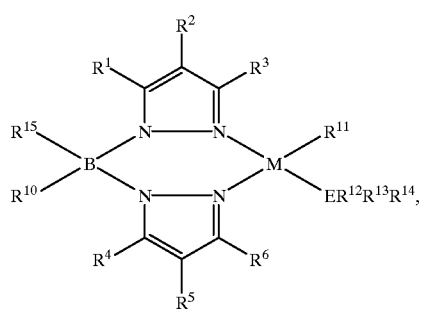

where

M is a metal from sub-group eight of the Periodic Table of the Elements,

E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and $R^{12}$ to $R^{14}$ are substituents selected from the group consisting of $C_1$- to $C_{30}$-organocarbon radicals and $C_3$- to $C_{30}$-organosilicon radicals.

5. A process for the preparation of oligomers and polymers of olefinically unsaturated compounds and of copolymers of olefinically unsaturated compounds and carbon monoxide by polymerizing the monomers at from 0 to 300° C. and from 1 to 500,000 kPa in the presence of a catalyst system comprising, as active constituents, A) a metal complex of the formula (I)

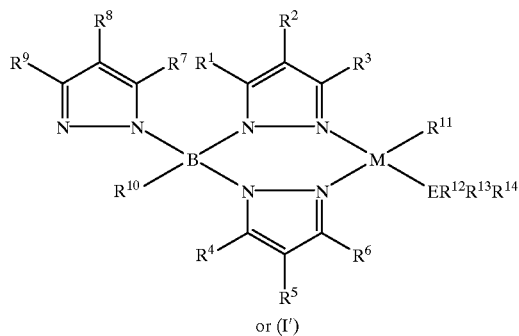

or (I')

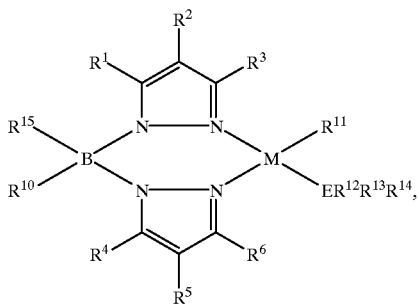

where

M is a metal from sub-group eight of the Periodic Table of the Elements,

E is an element from main group five of the Periodic Table of the Elements, $R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and $R^{12}$ to $R^{14}$ are substituents selected from the group consisting of $C_1$- to $C_{30}$-organocarbon radicals and $C_3$- to $C_{30}$-organosilicon radicals, and B) a Lewis acid.

6. A metal complex of the formula (I) or (I') which is suitable for the oligomerization and polymerization of olefinically unsaturated compounds and for the copolymerization thereof with carbon monoxide

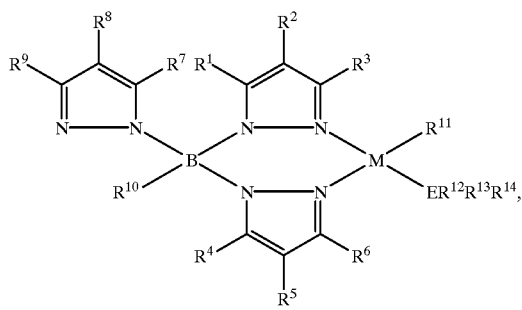

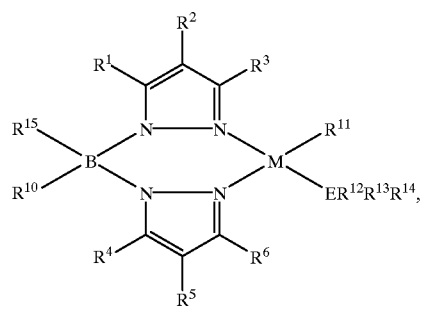

where
M is nickel,
E is an element from main group five of the Periodic Table of the Elements,
$R^1$ to $R^{11}$, $R^{15}$ are substituents selected from the group consisting of hydrogen, $C_1$- to $C_{30}$-organocarbon radicals and $C_3$- to $C_{30}$-organosilicon radicals, and
$R^{12}$ to $R^{14}$ are substituents selected from the group consisting of $C_1$- to $C_{30}$-organocarbon radicals and $C_3$- to $C_{30}$-organosilicon radicals.

7. A metal complex as claimed in claim 6, where $R^3$, $R^6$, $R^9$ and $R^{11}$ to $R^{14}$ are $C_6$- to $C_{20}$-aryl or $C_7$- to $C_{30}$-alkylaryl having 1 to 10 carbon atoms in the alkyl radical and 6 to 10 carbon atoms in the aryl radical, and $R^{10}$ and $R^{15}$ are hydrogen.

8. A metal complex of the formula (I) or (I') which is suitable for the oligomerization and polymerization of olefinically unsaturated compounds and for the copolymerization thereof with carbon monoxide

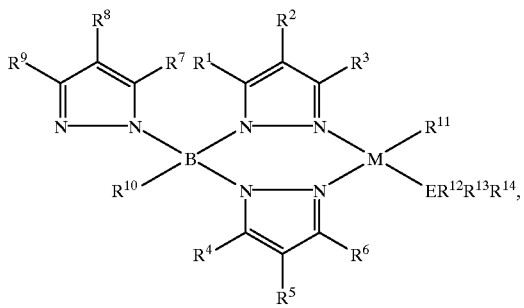

(I)

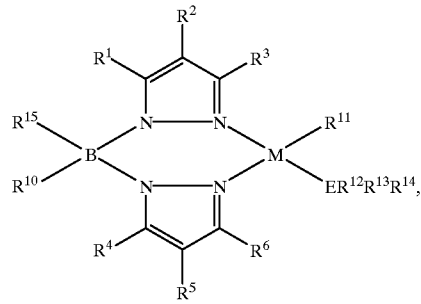

(I')

where
M is a metal from sub-group eight of the Periodic Table of the Elements,
E is an element from main group five of the Periodic Table of the Elements,
$R^1$ to $R^{10}$, $R^{15}$ are substituents selected from the group consisting of hydrogen, $C_1$- to $C_{30}$-organocarbon radicals and $C_3$- to $C_{30}$-organosilicon radicals,
$R^{11}$ is $C_6$- to $C_{20}$-aryl or $C_7$- to $C_{30}$-alkylaryl having 1 to 10 carbon atoms in the alkyl radical and 6 to 10 carbon atoms in the aryl radical, and
$R^{12}$ to $R^{14}$ are substituents selected from the group consisting of $C_1$- to $C_{30}$-organocarbon radicals and $C_3$- to $C_{30}$-organosilicon radicals.

9. A metal complex as claimed in claim 8, where $R^3$, $R^6$, $R^9$ and $R^{12}$ to $R^{14}$ are $C_6$- to $C_{20}$-aryl or $C_7$- to $C_{30}$-alkylaryl having 1 to 10 carbon atoms in the alkyl radical and 6 to 10 carbon atoms in the aryl radical, and $R^{10}$ and $R^{15}$ are hydrogen.

* * * * *